United States Patent [19]

Sinclair

[11] Patent Number: 5,587,381
[45] Date of Patent: Dec. 24, 1996

[54] METHOD FOR TERMINATING METHADONE MAINTENANCE THROUGH EXTINCTION OF THE OPIATE-TAKING RESPONSES

[76] Inventor: John D. Sinclair, Nokkalanniemi 7, SF-02230 Espoo, Finland

[21] Appl. No.: 410,529

[22] Filed: Mar. 27, 1995

[51] Int. Cl.$^6$ .......... A61K 31/485; A61K 31/44; A61K 31/135

[52] U.S. Cl. .......... 514/282; 514/295; 514/279; 514/289; 514/648

[58] Field of Search .................. 514/282, 295, 514/279, 289, 648

[56] References Cited

U.S. PATENT DOCUMENTS

| | | | |
|---|---|---|---|
| 3,493,657 | 2/1970 | Lewenstein | 424/260 |
| 3,773,955 | 11/1973 | Pachter et al. | 424/260 |
| 3,966,940 | 6/1976 | Pachter et al. | 424/260 |
| 4,767,764 | 8/1988 | Ciganek | 514/282 |
| 4,785,000 | 11/1988 | Kreek et al. | 514/282 |
| 4,882,335 | 11/1989 | Sinclair | 514/282 |
| 4,935,428 | 6/1990 | Lewis | 514/282 |
| 5,086,058 | 2/1992 | Sinclair et al. | 514/282 |
| 5,096,715 | 3/1992 | Sinclair | 424/449 |
| 5,272,149 | 12/1993 | Stalling | 514/255 |
| 5,472,943 | 12/1995 | Crain et al. | 514/12 |

*Primary Examiner*—Russell Travers
*Assistant Examiner*—William R. A. Jarvis
*Attorney, Agent, or Firm*—Ronald J. Kubovcik

[57] ABSTRACT

A method is provided for effectively terminating methadone maintenance therapy and the addiction to other legally-available opiates by selectively extinguishing the opiate-taking responses. Selective extinction is produced having sessions in which detoxified addicts make opiate-taking responses while an opiate antagonist blocks the positive reinforcement, interspersed by periods when the antagonist is absent and all responses except opiate-taking can be emitted. A similar method but with instructions not to take the opiate can subsequently be used to protect against resumption of illegal opiate use, or separately with patients addicted to illegal opiates producing reinforcement through the opioidergic system.

9 Claims, 3 Drawing Sheets

METHOD FOR TERMINATING METHADONE MAINTENANCE THROUGH EXTINCTION OF THE OPIATE-TAKING RESPONSES

FIELD OF THE INVENTION

The present invention relates to a treatment of opiate addiction in which the drug-taking responses of detoxified addicts are extinguished over a limited number of sessions by being emitted while the positive reinforcement is blocked by an opiate antagonist.

DESCRIPTION OF THE PRIOR ART

1. U.S. Pat. No. 3,493,657, which issued Feb. 3, 1970, describes a composition combining morphine and naloxone for parenteral use for providing a strong analgesic without "undesired or dangerous side effects."

2. U.S. Pat. No. 3,966,940, which issued Jun. 29, 1976, describes a composition combining methadone with a quantity of naloxone sufficient "to induce withdrawal symptoms when said composition is administered parenterally but insufficient to negate the action of said methadone when the composition is administered orally" to block the incentive for diverting the oral methadone composition to illicit parenteral use.

3. U.S. Pat. No. 4,882,335, which issued Nov. 21, 1989, describes a method for treating alcoholism in which the alcohol-drinking response is extinguished by being emitted while an opiate antagonists blocks the positive reinforcement from alcohol.

The applicant is of the opinion that the prior art neither teaches nor suggests the instant invention. The method for using the opiate antagonists, their dosages, and the purpose of the present invention are different from those in U.S. Pat. Nos. 3,493,657 and 3,966,940; the field of the instant invention and the specific methods involved are different from those of U.S. Pat. No. 4,882,335.

BACKGROUND OF THE INVENTION

Opiate addiction is a major health problem, with close to a million users in the United States. The traditional treatments attempt to increase the addict's will power to withstand the craving for opiates but do not decrease the craving itself. For a large percentage of addicts this is not sufficient: eventually they, give in to the craving and resume using the drugs.

The most successful treatment currently used is methadone maintenance therapy. It reduces mortality (Grönbladh et al., 1990) and social problems related to criminality (Ladewig, 1990). The relative success of this procedure is largely does to the fact that it does deal with the opiate craving. The craving is satisfied with a legally-prescribed opiate—methadone—and thus the patient has little motivation to obtain illegal opiates.

Unfortunately, methadone maintenance therapy has "a serious limitation . . . [because] clients have difficulty tapering off methadone" (Ladewig, 1990, p. 246). Clinicians, most addicts, and society in general would prefer that methadone maintenance were only a temporary phase for the patient, eventually replaced by a drug-free existence. This ideal, however, is seldom met, and for many addicts methadone maintenance appears to be a life-long program. There are other disadvantages to methadone maintenance therapy, including side-effects and illegal diversion of the methadone, but almost all of the disadvantages are caused by or increased by the lack of an effective method for terminating the therapy.

The present invention provides a safe and effective method for terminating methadone maintenance. After controlled withdrawal, the patient takes methadone while an opiate antagonists blocks positive reinforcement. As a result, the methadone-taking responses are extinguished and the craving for methadone is eliminated. An additional procedure is also provided to help guard against resumption of opiate use.

The present invention has the following significant advantages:

1. It is legally acceptable. Many years ago, A. Wikler among others speculated that heroin addiction might be treated with an extinction procedure involving opiate antagonists: "the narcotic antagonist-maintained patient, while still in the hospital . . . should be required to self-inject genuine, guaranteed pure heroin repeatedly" (Wikler, 1973, p. 615). Theoretically, the procedure almost certainly would be useful. Practically, however, it has never been used clinically. Probably a major reason why it has not been used is because it would be illegal. In the United States, heroin normally cannot legally be given to any patient. The practical difficulties and the feelings of most clinicians against allowing heroin self-administration in a treatment center have probably also help to keep the procedure from being used.

Permission has been obtained for experimental tests of Wikler's idea. Mello et al. (1981) found that naltrexone effectively suppressed heroin self-administration in an operant situation. A second study (see O'Brien et al., 1988) also found some evidence for suppression but was limited by dysphoria. The third study (Meyer, 1988) allowed patients to work for and obtain heroin in a treatment ward. Because of the setting, the procedure should not be expected to extinguish the previously learned opiate-taking responses and thus would not be very effective as a treatment, but it should extinguish opiate-taking in the ward. Half of the subjects did stop working for heroin almost completely after the first dose and showed a progressive decrease in craving. Although others continued to work for it, they also showed a progressive decrease in craving after the third day. However, because the patients did not show an "extinction burst", i.e., an initial increase in responding for heroin when the antagonist was first introduced, the author concluded that the data "did not appear to be consistent with models of operant extinction in the animal literature" (p. 164) and explained the results instead in terms of discriminative learning. The progressive decreases in craving, however, are not consistent with discriminative learning. Furthermore, an extinction burst is not always found in animal studies and especially not in animal studies with drug taking and opiate antagonists: no extinction bursts were found in rat studies with alcohol drinking (Sinclair, U.S. Pat. No. 4,882,335, 1989; Sinclair, 1990) which otherwise were always consistent with extinction, nor was one found by Davis and Smith (1974) in a study they felt showed extinction of opiate-seeking with naloxone in rats.

The legally-acceptable and practical method disclosed in the present invention, in which methadone is self-administered after an antagonist is given, has not previously been proposed. Furthermore, it should work even better than Wikler's method. Heroin is taken in a wide variety of situations. The methadone-taking response, however, needs to be extinguished primarily, or with many patients exclusively, in a single situation—at the treatment center where it has previously been given—and, from a practical viewpoint, this is an ideal situation for conducting extinction sessions.

2. It reduces craving and should be effective. Extinction requires that the opiate-seeking responses be made while reinforcement is blocked. The only way that opiate antagonists have previously been used in the treatment of opiate addiction is with a procedure designed to prevent all opiate use, "for maintenance of the drug-free state" (Jepsen. 1990, English abstract). For example, one clinical trial with 1005 addicts had the subjects being informed that because of the antagonist small doses of opiates would not produce pleasant effects, but large doses could be fatal (Renault, 1980). Although extinction is sometimes mentioned in the rationale for such studies, the actual procedure prevents extinction in all subjects who obey the instructions. Opiate antagonists alone do not reduce the craving for opiates nor does simply knowing that taking opiates will not produce euphoria. Most of the subjects in the Renault study dropped out, and there were no significant benefits. Other studies have shown that although the procedure is better than the traditional procedures in highly motivated subjects, it is not as effective as methadone maintenance therapy (Jepsen, 1990). As Frank H. Gawin stated recently (quoted by M. Holloway, 1991): "Just blocking the euphoria is not the panacea that some naive individuals think it is."

Extinction, however, does reduce craving. In the Renault study, 17 patients disobeyed instructions and, as required for extinction, took opiates while on naltrexone. These patients showed significant improvement and reduction in reported craving.

3. It closely reproduces during extinction the stimulus situation to which opiate-taking had been learned. A form of extinction without antagonists, called "cue exposure", has subjects being presented with the external stimuli related to drug taking and/or making the preparatory responses for self-administration of a drug, but not actually taking the drug. (e.g., G. A. Marlatt, 1990; O'Brien et al., 1990). The physical controls to prevent drug taking, however, inevitably change the situation for the subject, thus reducing the effectiveness of extinction. These controls are not needed in the present invention because an opiate antagonist is used instead to prevent reinforcement.

The antagonist may produce another advantage over cue exposure. Opiate-seeking responses probably are reinforced not only from the opiates self-administered but also partly from the thrill and stimulation involved in the procurement and taking of the drug. The possibility that this additional reinforcement might also be mediated by the opioidergic system is suggested by findings that the reinforcement from other forms of stimulation—e.g., from pleasant tastes, physical exertion, and sexually-related stimuli—is controlled by the system. (In experiments, e.g., saccharin drinking was apparently extinguished with naloxone.) Stimuli previously associated with opiates may gain the ability to activate the opioidergic system and thereby also produce additional reinforcement. The opiate antagonist in the present invention would block this additional reinforcement, but cue exposure would not.

4. It is medically safe. The only previous proposal for a practical method for extinguishing a drug-taking response with opiate antagonists is earlier patent (Sinclair, U.S. Pat. No. 4,882,335, 1989). This was for the treatment of alcoholism rather than opiate addiction and thus differs in many ways from the present invention. Of most importance, the alcoholism treatment must begin while the subjects are still physiologically dependent in order to avoid the giving alcohol to withdrawn alcoholics forbidden by ethical guidelines. This procedure, however, would be medically very dangerous for opiate addicts because the antagonist would cause precipitous withdrawal.

5. It includes a process referred to herein as "selective extinction". The probability that an opiate-seeking response will be emitted is not determined by the absolute strength of the response but rather by its strength relative to all competing responses. Some of the competing responses (e.g., eating highly palatable foods) are also reinforced by the opioidergic system. Keeping an addict continually on an opiate antagonist would extinguish these competing responses, thus reducing the relative effect of weakening the opiate-seeking response. Nevertheless, a major goal in the past and today (Holloway, 1991) has been preparations such as naltrexone implants that would keep patients continually under the influence of an antagonists for weeks or months after a single administration. Advocates of extinction also failed to see the problem: e.g., Wikler (1973) wrote that the patient should be maintained continually on the narcotic-antagonist for a year.

The present invention is not dependent upon the eventual development of sustained-release preparations; indeed they would be counterproductive. The selective extinction procedure intersperses extinction sessions when the major activity is opiate-seeking behavior with periods when the patient is free of antagonist and able to make all responses except for opiate-seeking. Any competing responses that happen to be weakened during the extinction sessions are strengthened when they are emitted and reinforced during the intervening periods. Thus it changes extinction with antagonists from being a crude method with broad behavioral effects into a precise tool for removing only a specific response.

Selective extinction also has the advantage that it should minimize adverse side-effects from the antagonists. For example, problems from the liver toxicity of naltrexone develop only after prolonged continual administration (Morgen and Kosten, 1990). Further, the dysphoria reported by some patients maintained on naltrexone, which may contribute to high drop-out rates, may be caused by the antagonist continually blocking many sources of pleasure, and should be reduced if in selective extinction since they are free to enjoy other opioidergically-reinforced activities other than opiate-seeking.

SUMMARY OF THE INVENTION

The present invention contemplates a therapeutic method, utilizing the ability of opiate antagonists to block the positive reinforcement produced by taking opiates and also from various forms of stimulation, to extinguish the primary opiate-taking response and the responses made in preparation for opiate-taking.

The method has two modes which can be used separately or sequentially. The first mode extinguishes the taking of a legally-available opiate agonist such as methadone, thus solving the "serious limitation" of methadone maintenance therapy by helping the patient safely terminate methadone use. A patient with active opiate addiction is first withdrawn from the legal opiate in order to prevent precipitous withdraw with subsequent administration of an opiate antagonist, under conditions precluding the use of all opiates. This is followed by a series of extinction sessions in which the addict has an antagonist administered and then takes the legal opiate under conditions similar to those in which it had previously been taken. Extinction sessions are separated by periods in which the patient is free of antagonist, cannot take opiates but can make all other responses. The procedure selectively weakens the strong opiate-seeking responses without permanently weakening other competing responses.

The second mode has a detoxified patient take an opiate antagonist and then go through the preparatory responses for opiate-taking in surroundings similar to those in which the responses were learned, but with instructions not to take the opiate itself. The antagonist provides protection in case the patient disobeys instructions and does proceed to take the opiate; the experience is then a regular extinction session which will weaken the responses. Because of this protection, external supervision and controls to prevent opiate taking are not necessary; the situation is thus more realistic than with cue exposure methods, making extinction more effective. An additional possible advantage is that the antagonist would block inherent or conditioned reinforcement from activation of the endogenous opioidergic system, and thus promote better extinction of the preparatory responses than cue exposure alone.

The extinction procedure in a limited period of time weakens the opiate-seeking responses and the corresponding craving for methadone, thus providing a secure means for terminating methadone maintenance therapy, and thereby improving the acceptability of such programs while reducing the disadvantages inherent in continual maintenance. It also provides a means for extinguishing the taking of other legally-available opiates.

The second mode used alone improves the safety and effectiveness of cue exposure procedures. It can be employed with illegal opiates such as heroin and also with other illegal drugs that produce reinforcement through the opioidergic system in the brain, such as cocaine, d-amphetamine, phencyclidine, and MDMA.

DESCRIPTION OF PREFERRED EMBODIMENTS

Figure 1:
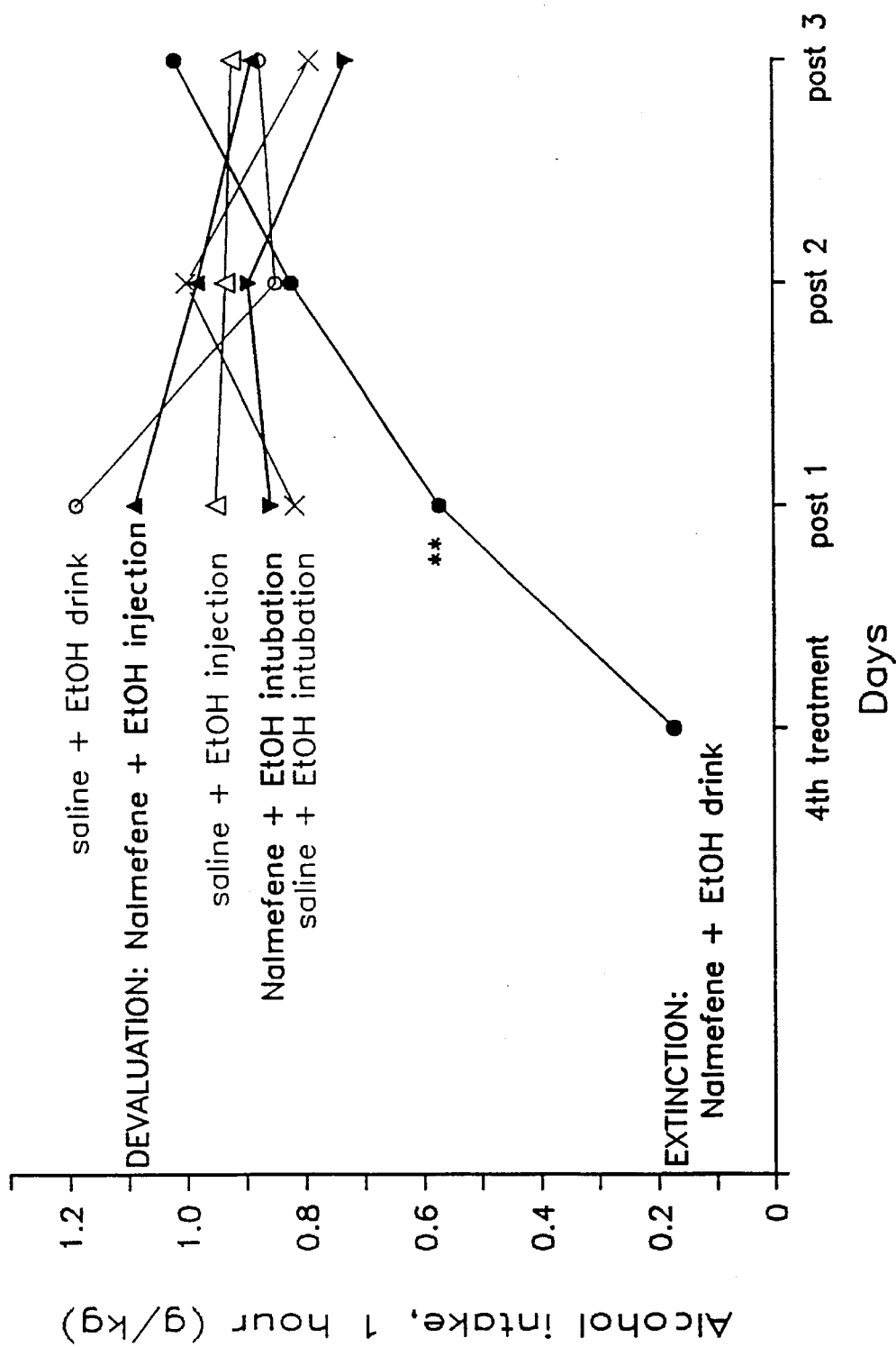
FIG. 1 shows the suppression of alcohol drinking after a treatment designed to produce extinction (drinking ethanol, EtOH, while on nalmefene) and the lack of suppression after a treatment designed to produce devaluation (being injected with ethanol while on nalmefene). Being intubated with ethanol while on nalmefene, which produces some of the stimuli to which alcohol drinking was previously learned, produced intermediate aftereffects, as predicted by the extinction hypothesis. ** indicates significantly ($p<0.01$) lower alcohol drinking by the EXTINCTION group than by their controls (saline+EtOH drink), than by the DEVALUATION group, and by all 5 other groups combined.

The extinction procedures here can be used to treat all addicts to opiate agonists. The particular mode employed and the details of its use differ according to the type of addiction. The first mode is for patients with an active addition to a legal opiate. Most commonly this would be patients on methadone maintenance therapy, but it also could include patients being maintained on any other agonists or partial agonists (e.g., buprenorphine) which are currently legal for substitution-drug treatment of opiate addiction. With ethical approval, this mode might also be used with patients addicted to morphine and other opiate agonists that can legally be prescribed but are not used for maintenance therapy.

The patients must first be withdrawn from opiates to prevent subsequent precipitous withdrawal when an opiate antagonist is given. Withdrawal could be accomplished with the usual methods to ensure the patient's health. During this period, care must be taken to prevent the patient from obtaining opiates from any other source as well. Before beginning the extinction procedure, the completeness of withdraw should be tested with low doses of an antagonist. This testing could be done with daily administrations with an antagonist starting with a dose far lower than that needed to precipitate withdrawal and increasing progressively each day until a dose equivalent to that to be used in extinction is administered.

The first extinction session can be conducted as soon as it is ascertained that the antagonist will not be precipitate withdrawal. It should be made under close medical supervision. The patient should be given the antagonist and then after sufficient delay to permit active quantities to be in the brain, the patient should take methadone (or other legal opiate to which he or she was addicted) in the manner to which it had previously been taken.

Subsequent extinction sessions should be conducted in surroundings matching those in which methadone (or other legal opiate) previously had typically been taken. For example, if the patient had sometimes previously been given take-home doses of methadone, the extinction sessions should also include ones with take-home methadone.

The extinction sessions should be interspersed with periods when the patient is free of the antagonist and able to make all responses except those related to opiate taking. Active programs for learning alternative responses and living a drug-free life could be conducted during these periods. Care must be taken that no opiates are used. There should be no problem, however, with renewed withdrawal symptoms because taking opiates in the presence of an antagonist does not induce physiological dependence. Alternatively, the antagonist-free period without access to opiates could be after completion of extinction, although theoretically this should be less effective than interspersing such periods between extinction sessions.

The number of extinction sessions needed will depend upon the severity of the addiction and the variety of situations in which the legal opiate had been taken. Few extinction sessions— perhaps only 3 or 4—would be needed for termination of a methadone maintenance therapy in which methadone always had been taken in only one situation (e.g., at the treatment center).

After the final session the patient would be told to abstain completely from opiates. A variety of programs to increase the will power and incentive to abstain and to resume a normal life could be also used in conjunction with the extinction procedure.

The first mode of the extinction procedure should weaken the responses and the craving for taking methadone (or other legal opiate) sufficiently for patients to cope with them successfully. There is, however, the potential problem that in some patients extinction of methadone-taking response might uncover the previously learned response involved in taking illegal opiates. This problem should be greater in those patients who had had a longer history of using illegal opiates prior to being switched to methadone, who had been on methadone for shorter periods, and who had been less successful in establishing a normal, productive life style away from situations associated with illegal drug use while on methadone. The second mode of the extinction procedure guards against the resumption of illegal opiate use.

In the second mode, the patient is given an opiate antagonist and while it is active, goes through the preparatory responses for opiate taking that had previously been learned, but with instructions not to actually self-administer the opiate. (referred to herein as a "cue extinction session".) The specific responses will, of course, depend upon which opiate or opiates had previously been used, the route by which they had been taken, and the responses previously used in their procurement. Cue extinction sessions will be interspersed (or followed) by periods free of antagonist when opiates cannot be used, in order to provide selective extinction.

The cue extinction sessions could be done under controlled conditions, similar to those used in the cue exposure procedure, to prevent actual use of opiates. Since the situation and the patients feelings in it will unavoidably differ somewhat from those to which opiate-seeking behavior had been previously learned, this may not be sufficient to protect some patients against resumption of opiate use.

As additional protection, the patient leaving the treatment center will be advised that if opiate craving is present, or situations previously associated with opiate use are likely to be encountered, he (or she) should take an antagonist. This could be a take-home dose of antagonist, or the patient could return to the treatment center to get the antagonist. The patient is still under instructions not to take opiates, but the importance is emphasized of taking an antagonist whenever there is chance of stimuli associated with opiates or the availability of opiates themselves.

After taking the antagonist, if the patient encounters opiate-related stimuli or makes opiate-seeking responses, but does not take the opiate, this amounts to a cue extinction session under realistic conditions. If the patient disobeys instructions and does take the opiate, this amounts to a regular extinction session. In either case, the patient is protected from getting reinforcement from either the stimuli involved in the preparatory steps and from the presence of opiates in the brain, and thus opiate-seeking behavior is not relearned, but rather weakened further.

The second mode could be used separately for patients having a current addiction to an illegal opiate. The patient would first have to undergo detoxification and then the tests to ascertain that the antagonist would not still produce precipitous withdrawal. Alternatively, such patients could first be switched to methadone maintenance therapy for a period of time, and then given the first, then second modes of the extinction procedure. With ethical approval, a variation of the first mode could also be used directly for such patients: after detoxification the patient would have extinction sessions with an opiate antagonist and a legally-available opiate self-administered in the same manner that the patient previously took the illegal opiate. For example, an intravenous heroin user could have extinction sessions with intravenous morphine.

The second mode could also be used separately for treatment of addiction to other illegal compounds that produce their reinforcement whole or partially through the opioidergic system. A method for distinguishing such drugs is to see if an opiate antagonist suppresses their ability to lower the threshold for rewarding electrical intracranial self-stimulation (ICSS) (see Bain and Kornetsky, 1990). Compounds currently shown to have this ability are cocaine (Bain and Kornetsky, 1987), d-amphetamine (Holtzman, 1980a: Esposito et al., 1980), phencyclidine (PCP) (Kornetsky et al., 1981), and ecstasy (MDMA) (Hubner et al., 1988). It has also been shown that cocaine influences beta-endorphin levels and release (Forman and Estilow, 1988), and opioids have discriminative effects similar to phencyclidine (Holtzman, 1980b). Although earlier studies had obtained mixed results, the most recent experiment (Mello et al., 1990) found that naltrexone produced a significant suppression of cocaine self-administration in rhesus monkeys. The weaker results with cocaine than with alcohol or opiates might be due only to procedural differences but they could be caused by cocaine having other sources of reinforcement in addition to the opioidergic system. In the latter case, complete extinction could be produced only by combining an opiate antagonist with a blocker for the other reinforcing effects, but even a partial extinction with only the opiate antagonist should be useful therapeutically.

The second mode can also be used with patients who combine opiates with one of these other drugs, e.g., "speedballing", by combining opioid agonists with cocaine. A preliminary non-controlled clinical study (Kosten et al., 1989) found positive results with naltrexone with such patients, although its procedure was not designed to optimize extinction.

Examples of opiate antagonists include nalmefene, naltrexone, naloxone, cyclazocinc, diprenorphine, etazocine, levalorphan, metazocine, nalorphine, and their salts. The preferred opiate antagonists are nalmefene, naltrexone, and naloxone, which have been shown to be safe for use in humans and free of severe side-effects. All three are pure antagonists with no addiction potential of their own. The preferred oral dose range for nalmefene is 1 to 10 mg daily, for naltrexone 10 to 200 mg daily. Naloxone is usually given by injection, and the preferred dose range would be 0.4 to 10 mg daily. The exact dose used will depend upon the weight of the patient, but must be sufficient to block central opiate effects throughout a single extinction session.

Examples of routes of administration for the antagonist are oral consumption in any form, injection, transdermal administration, slow-release injection, nasal administration, sublingual administration, implantable drug delivery depots, and the like. A non-obtrusive, non-painful route would be preferable. Routes that allow the patient to become free of active quantities of antagonist in a short period of time are preferred for the selective extinction method.

The feasibility of the present invention is further illustrated by the following example.

EXAMPLE 1

The present invention is possible only if drug-taking responses can actually be extinguished by being emitted while on an opiate antagonist. Extinction is well-established for conditioned reflexes (e.g., salivation) and instrumentally learned responses (e.g., lever pressing) when reinforcement is prevented externally simply by removing a source of reward (e.g., not giving food). One reason perhaps why the cue exposure procedure has readily gained theoretical acceptance in the field is that it too has reinforcement being prevented externally, by not allowing the drug to be self-administered.

In the present invention, however, reinforcement is prevented in a different manner: it is blocked, not externally, but rather internally, by the pharmacological actions of the antagonist in the central nervous system.

The clinical results cited earlier (Renault, 1980), in which patients taking opiates while on naltrexone showed significant improvement, were consistent with this form of extinction, but there are other possible explanations. Similarly, an early, study (Davis and Smith, 1974) in which naloxone pretreatment progressively decreased lever pressing by rats for intravenous infusions of morphine, is consistent with extinction, but again there are other possible explanations.

The only way to make a convincing case that such extinction actually occurs is to undertake a systematic program of experiments, testing and eliminating every other hypothesis imaginable. This is what the applicant has now done for the effect of opiate antagonists on alcohol drinking. The Example here is part of this program.

Previous experiments (Sinclair, U.S. Pat. No. 4,882,335, 1989; Sinclair, 1990) had eliminated all of the alternative hypotheses with which the applicant was familiar. When these results were presented in 1994, however, some clinicians remained skeptical that extinction with opiate antagonists was responsible and pointed out a hypothesis, involving a process they called "devaluation", which could account for all of the applicant's previous results and also for those cited above by Renault (1980) and Davis and Smith (1974).

Devaluation, unlike extinction, does not require that the response be emitted or that stimuli to which the response has been learned are present; instead it predicts that merely having alcohol in the body after administration of an opiate antagonist should suppress subsequent alcohol drinking.

The experiment here tested the devaluation and extinction hypotheses. Thirty-six male Wistar rats with an initial mean weight of 304±7 (SE) g were given continual access to 10% alcohol in one bottle and water in a second for 4 weeks, then switched to having alcohol access only 1 hour per day but continual water access. After 12 days of 1 hr access, the rats were divided into 6 groups matched for alcohol intake in the last 5 days. The "EXTINCTION" group was injected subcutaneously with an antagonist, nalmefene (0.36 mg/kg), 20 min before being allowed to drink alcohol on each of the next 4 days. This greatly reduced their alcohol drinking, as shown for the "4th treatment" day in FIG. 1.

The "DEVALUATION" group was injected intraperitoneally with alcohol after nalmefene on each of the 4 treatment days. A yoke-control procedure was used: each animal was matched with one in the EXTINCTION group on the basis of prior alcohol drinking and then on each treatment day was injected with the quantity of alcohol drunk by that animal on that day. Another group was intubated with the same amounts of alcohol after nalmefene, thus although not making the response, still experiencing some of the stimuli—the feeling of alcohol in the stomach and perhaps some of the taste—that had been present when alcohol drinking was learned. Three control groups had saline rather than nalmefene injections prior to injection or intubation with alcohol or being allowed to drink the quantity alcohol consumed by their yoked pairs in the EXTINCTION group.

The important data is on the first day after the end of treatment ("post 1" in FIG. 1) when all groups were injected with saline and then allowed to drink alcohol freely for 1 h. Devaluation predicts that all three groups given nalmefene should drink the same amount and all three should drink less than their respective control groups. Extinction predicts that the EXTINCTION group should drink the least, the DEVALUATION group should drink the most, and the Nalmefene+EtOH intubation group should drink an intermediary amount.

The results (FIG. 1) are contrary to devaluation but match the all predictions of the extinction hypothesis. The DEVALUATION group did not drink less than their control group (saline+EtOH injection) but rather tended to drink more alcohol. The three nalmefene groups did not drink similar amounts. Instead, the EXTINCTION group drank significantly less alcohol than the their control group (saline+EtOH drink) and significantly less than the DEVALUATION group. The intake by the Nalmefene+EtOH intubation group was midway between the other nalmefene groups.

These results together with those from all the previous experiments in the series provide strong evidence that alcohol drinking can be extinguished by emitting it in the presence of an opiate antagonist. Since there is no doubt that the reinforcement from opiates is also blocked by opiate antagonists, the results also indicate that opiate-seeking behavior could be extinguished by being emitted in the presence of an opiate antagonist.

EXAMPLE 2

The effect of the opiate antagonist, nalmefene, on oral methadone self-administration was tested in rats. This, however, first required development of an animal model of methadone drinking. Although animals will self-administer opiates intravenously and will drink opiates in the absence of other fluids, the bitter taste of most opiates including methadone has previously precluded free-choice models of oral opiate self-administration.

The feasibility of such a model was suggested by a study (Hyytiä and Sinclair, 1993) with rats of the AA line selectively developed in the applicant's laboratory for high voluntary alcohol consumption. Consistent with previous conclusions that these rats consume more alcohol at least partly because they receive more opioidergic reinforcement, when provided with a continual choice between water in one bottle and solutions of the potent opiate agonist, etonitazene, in the other, the AA rats voluntarily drank pharmacologically-active quantities of etonitazene and consumed significantly more etonitazene than did either rats of the ANA line developed for low alcohol intake or normal Wistar rats.

This procedure was next extended to one in which access to etonitazene solution was limited to 1 hr daily. This is similar to the limited access procedure developed for alcohol drinking (Sinclair et al., 1992) and has several advantages over continual access procedures. For example, since the animals always have food and water available and normally would be consuming almost none of either during any particular daytime hour, if the animals do consume alcohol or a drug at this time, it is not because they arc thirsty or hungry. The limited access procedure also minimizes interference from physiological dependence; no evidence of opiate withdrawal was observed in this study with or without opiate antagonist treatment.

Male 12 male AA rats (n=12) of the $F_{64}$ generation, at the age of 2 months were given free access to 10% alcohol plus food and water in individual cages, and then after 5 months of alcohol drinking were switched from alcohol for one day to continual access to etonitazene solution (1 μg/ml). Subsequently, for 4 weeks the animals had access to etonitazene from 10:00 to 11:00 daily. During the last 5 days subcutaneous saline injections were made 20 minutes prior to access. Then the animals were divided into 2 equal groups matched for the "before" intake during these 5 days: one group continued to receive saline and the other obtaining 0.18 mg/kg nalmefene (subcutaneously, in a volume of 1 ml/kg) before access.

Figure 2:
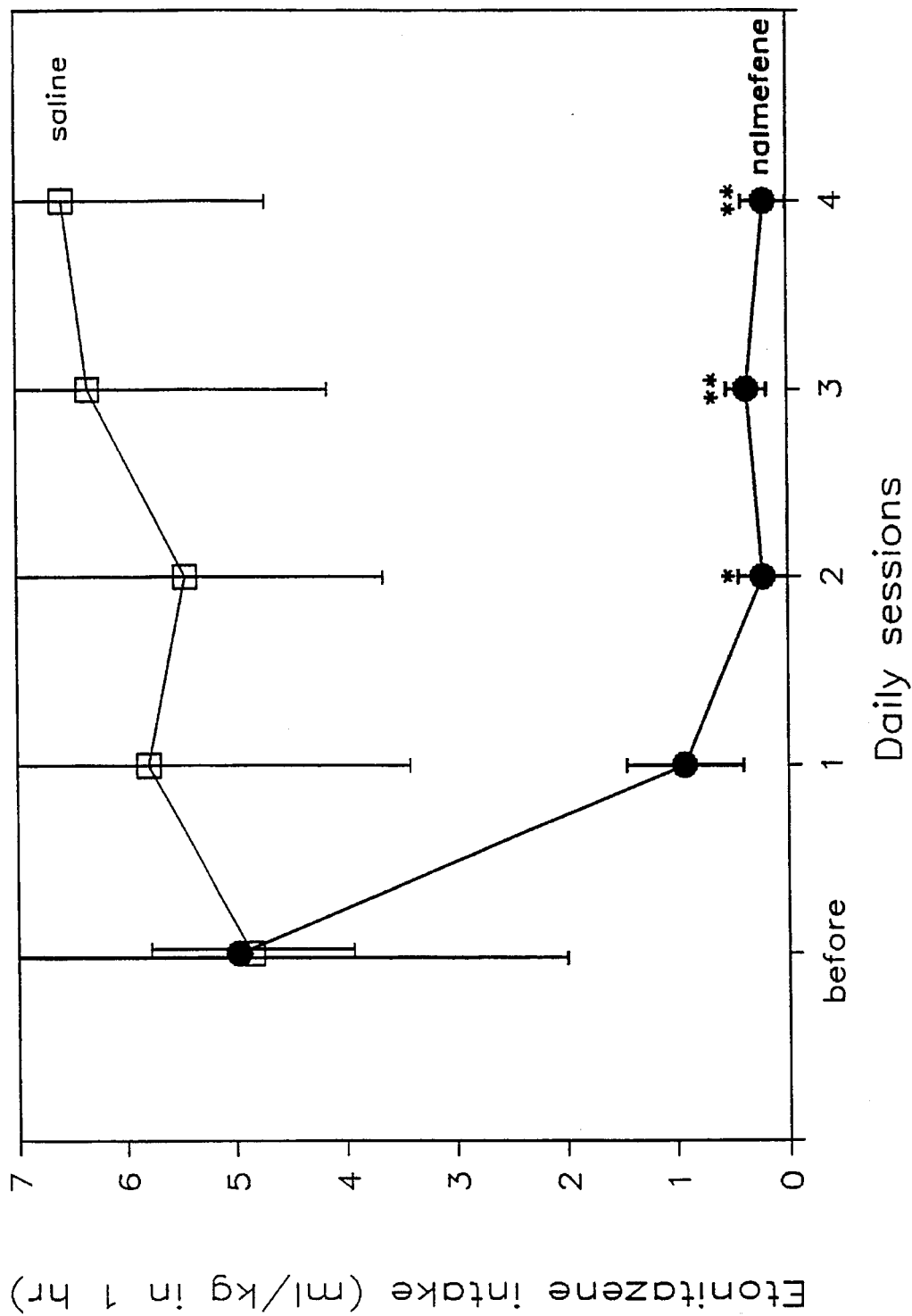
FIG. 2 shows the suppression of the drinking of etonitazene (a potent opiate agonist) caused by nalmefene. The rats were of the AA line developed by genetic selection for high alcohol drinking, and also found to have a high disposition for self-administration of opiates. Etonitazene was available 1 hr daily. Nalmefene (0.18 mg/kg) injected subcutaneous to 6 of the rats 20 min prior to access nearly abolished etonitazene drinking. *$p<0.05$, **$p<0.01$ significantly different from saline controls.

Nalmefene was very effective in suppressing etonitazene drinking (FIG. 2). The pattern across daily sessions was similar to that obtained previously (e.g., in Example 1 here) in other animals with alcohol drinking. Etonitazene intake was not significantly suppressed during the 1st daily session after nalmefene (because of larger standard errors in the saline controls, all statistical comparisons were made with the nonparametric Mann-Whitney test: U=8.5, corrected for ties, p=0.128). The nalmefene pretreated rats drank significantly less etonitazene in the 2nd session (U=4.5, p=0.031), and by the third and fourth nalmefene sessions the difference was highly significant (both sessions:U=1, p=0.006). During the 4th session only one of the 6 nalmefene rats drank a measurable amount.

The opiate of practical interest, however, was not etonitazene but rather methadone. Consequently, the animals were shifted to methadone for 5 days, but because intake fell they were put back on etonitazene. After intake recovered, they were given daily 1 hour access to solutions of 1 μg/ml etonitazene with increasing methadone concentrations, then to etonitazene-methadone solutions with decreasing etonitazene concentrations, and finally to methadone (40 μg/ml) alone.

Although more variability was observed with methadone than etonitazene, the mean volume of methadone consumption was similar to that with etonitazene (compare FIGS. 2 and 3), and most of the AA rats did drink methadone and drank relatively consistent amounts during each daily session. Typically, the rats would come to the front of the cage and begin drinking methadone when the bottle was first made available; a second bout of methadone drinking frequently took place near the end of the access hour. The rats previously treated with nalmefene tended to be lower than the controls during the 5 days on methadone but by the end of the 3 weeks the two group were again very similar.

The animals were injected once with saline before methadone access and then divided into 2 groups: one continued to receive saline and the other received 0.18 mg/kg nalmefene 20 min before the next 4 daily methadone sessions. Of the 6 rats now treated with nalmefene 2 had previously received nalmefene and 4 saline in the test on etonitazene drinking.

Figure 3:
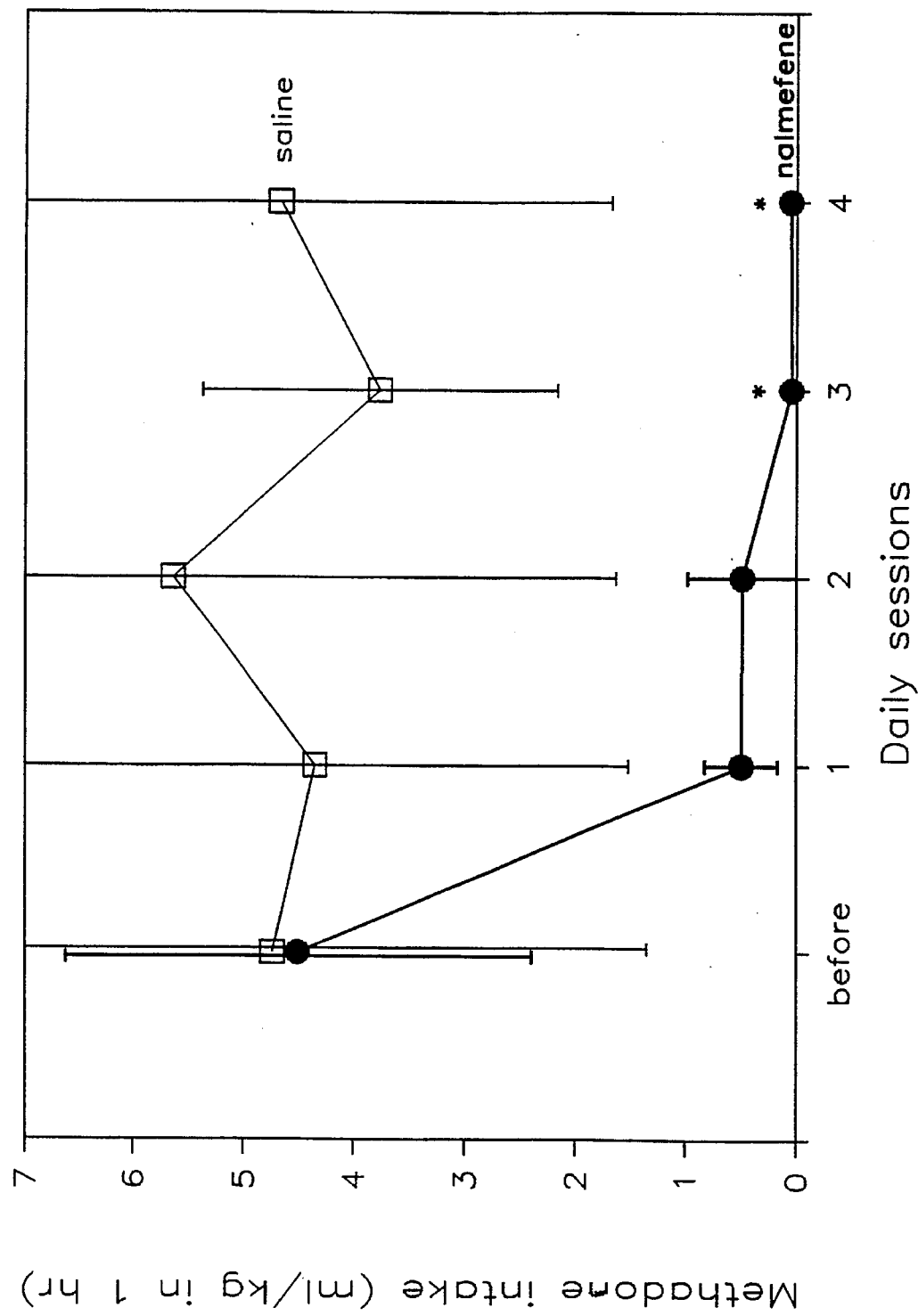
FIG. 3 shows the suppression of methadone drinking in AA rats by nalmefene. *$p=0.02$.

Nalmefene had a profound effect on methadone drinking and eventually abolished it almost completely (FIG. 3). The change in methadone drinking over all 4 days (relative to the preceding saline-injection "before" day) was significantly greater in the nalmefene-treated rats than in the saline controls (U=4, p=0.025). As with etonitazene, there was no significant effect on the first nalmefene day (U=9, p=0.150) but on both the 3rd and 4th sessions the nalmefene-treated rats had significantly lower methadone intakes than the controls (both: U=3.5, p=0.020). In these sessions, 5 of the 6 nalmefene pretreated rats drank no methadone and the remaining animal took only a minimal amount.

I claim:

1. A method for terminating methadone maintenance therapy and addiction to other legally-available opiates by selective extinction of the opiate-taking response, comprising the steps of:

withholding all opiates from a subject suffering from addiction to a legally-available opiate for a sufficient time to prevent an opiate antagonist when administered to the subject from causing precipitous withdrawal; and thereafter administering to the subject an opiate antagonist selected from the group consisting of nalmefene, naltrexone, naloxone, cyclazocine, etazocine, levallorphan, metazocine, nalorphine, and salts thereof in a daily dosage sufficient to block the effects of opiate agonists;

while the amount of the antagonist in the subject's body is sufficient to block opiate effects, having the subject self-administer the legally-available opiate agonist to which he or she is addicted;

withholding the opiate antagonist from the subject;

when the amount of antagonist is no longer sufficient to block opiate effects, not allowing the subject to self-administer opiates; and continuing the above steps of administration of the opiate antagonist and the subject's taking of the opiate and the withholding of the antagonist for a period when the subject cannot take opiates until the opiate-taking behavior is extinguished.

2. A method for treating opiate addiction through selective extinction, comprising the steps of:

repeatedly administering to a subject, suffering from opiate addiction but not physiologically dependent upon opiates, an opiate antagonist selected from the group consisting of nalmefene, naltrexone, naloxone, cyclazocine, etazocine, levallorphan, metazocine, nalorphine, and salts thereof in a daily dosage sufficient to block the effects of opiate agonists;

while the amount of the antagonist in the subject's body is sufficient to block opiate effects, having the subject make the responses the subject has usually made in the past in preparation for self-administration of an opiate but with instructions not to self-administer an opiate;

withholding the antagonist from the subject;

when the amount of antagonist is no longer sufficient to block opiate effects, not allowing the subject to make the preparatory responses but continuing instructions not to self-administer an opiate; and continuing the above steps of administration of the opiate antagonist and making the preparatory responses and the period free of the antagonist when preparatory responses and opiate-taking responses cannot be made until these responses are extinguished.

3. A method for terminating methadone maintenance therapy and addiction to other legally-available opiates and for treating addiction to illegal opiates in the same subject by selective extinction of the responses of taking the legally-available opiate and selective extinction of the responses made in preparation for taking the illegal opiate, comprising the steps of:

withholding all opiates from a subject suffering from addiction to a legally-available opiate for a sufficient time to prevent an opiate antagonist when administered to the subject from causing precipitous withdrawal; and thereafter administering to the subject an opiate antagonist selected from the group consisting of nalmefene, naltrexone, naloxone, cyclazocine, diprenorphine, etazocine, levallorphan, metazocine, nalorphine, and salts thereof in a daily dosage sufficient to block the effects of opiate agonists;

while the amount of the antagonist in the subject's body is sufficient to block opiate effects, having the subject self-administer the legally-available opiate agonist to which he or she is addicted;

withholding the opiate antagonist from the subject;

when the amount of antagonist is no longer sufficient to block opiate effects, not allowing the subject to self-administer opiates; and continuing the above steps of administration of the opiate antagonist and the subject's taking of the legally-available opiate agonist and the withholding of the antagonist for a period when the subject cannot take opiates until the opiate-taking behavior is extinguished; and thereafter repeatedly administering to the subject said opiate antagonist;

while the amount of antagonist in the subject's body is sufficient to block opiate effects, having the subject make the responses the subject had usually made in the past in preparation for self-administration of an illegal opiate but with instructions not to self-administer an opiate;

withholding the antagonist from the subject;

when the amount of antagonist is no longer sufficient to block opiate effects, not allowing the subject to make the preparatory responses but continuing instructions not to self-administer an opiate; and continuing the above steps of administration of the opiate antagonist and making the preparatory responses and the period free of the antagonist when preparatory responses and opiate-taking responses cannot be made until these responses are extinguished.

4. The method in accordance with claim 1, 2 or 3 wherein the opiate antagonist is nalmefene.

5. The method in accordance with claim 4 wherein nalmefene is given in doses from 0.1 to 300 mg daily.

6. The method in accordance with claim 1, 2 or 3 wherein the opiate antagonist is naltrexone.

7. The method in accordance with claim 6 wherein naltrexone is given in doses from 10 to 300 mg daily.

8. The method in accordance with claim 1, 2 or 3 wherein the opiate antagonist is naloxone.

9. The method in accordance with claim 8 wherein naloxone is given in doses from 0.2 to 30 mg daily.

\* \* \* \* \*